(12) United States Patent
Sabti

(10) Patent No.: US 8,419,790 B1
(45) Date of Patent: Apr. 16, 2013

(54) INTRAOCULAR LENS FIXATION DEVICE

(76) Inventor: Khalid Sabti, Safat (KW)

( * ) Notice: Subject to any disclaimer, the term of this patent is extended or adjusted under 35 U.S.C. 154(b) by 0 days.

(21) Appl. No.: 13/603,244

(22) Filed: Sep. 4, 2012

(51) Int. Cl.
  *A61F 2/16* (2006.01)
  *A61F 9/00* (2006.01)

(52) U.S. Cl.
  USPC .......................................... 623/6.12; 606/107

(58) Field of Classification Search ................. 623/6.12, 623/6.39, 907; 606/107, 166; 296/1.2; 600/37, 600/205
  See application file for complete search history.

(56) References Cited

U.S. PATENT DOCUMENTS

| | | | |
|---|---|---|---|
| 4,047,532 A * | 9/1977 | Phillips et al. ................. | 606/107 |
| 4,332,408 A | 6/1982 | Cointment | |
| 4,406,285 A | 9/1983 | Villasenor et al. | |
| 4,688,570 A | 8/1987 | Kramer et al. | |
| 6,273,894 B1 | 8/2001 | Dykes | |
| 6,394,948 B1 * | 5/2002 | Borst et al. ...................... | 600/37 |
| 6,596,000 B2 | 7/2003 | Chan et al. | |
| 6,730,020 B2 * | 5/2004 | Peng et al. ..................... | 600/201 |
| 7,476,199 B2 * | 1/2009 | Spence et al. .................. | 600/210 |
| 2002/0042616 A1 | 4/2002 | Chan et al. | |
| 2004/0097955 A1 | 5/2004 | Feingold | |
| 2011/0071524 A1 | 3/2011 | Keller | |

FOREIGN PATENT DOCUMENTS

WO    WO 2011/155922 A1    12/2011

* cited by examiner

*Primary Examiner* — Gary Jackson
*Assistant Examiner* — Lindsey Bachman
(74) *Attorney, Agent, or Firm* — Richard C. Litman

(57) ABSTRACT

The intraocular lens (IOL) fixation device includes an elongate handle having a slender, elongate neck extending therefrom. The neck terminates at a head section. The head section includes a rotator, upon which a plurality of radiating vacuum holding legs extends outward, the end of each leg having a suction cup attached thereto. The legs and the suction cups include hollow channels that communicate with a source of vacuum in order to facilitate gripping of the IOL. Upon insertion of the IOL and proper placement of the head over the IOL, activation of vacuum firmly holds the IOL through the suction cups. The rotator is rotated to accurately align the IOL within the capsular bag. The IOL fixation device also includes irrigation means for selective irrigation of the target area.

12 Claims, 6 Drawing Sheets

INTRAOCULAR LENS FIXATION DEVICE

BACKGROUND OF THE INVENTION

1. Field of the Invention

The present invention relates to ophthalmic surgery, and particularly to an intraocular lens fixation device that provides precise, accurate alignment of an intraocular lens with minimal risk during the ophthalmic surgical procedure.

2. Description of the Related Art

An intraocular lens (IOL) is a synthetic lens used to correct various eye-related impairments, such as cataracts, astigmatism, and refractive errors. The impaired crystalline lens in the eye is replaced by the IOL through implant surgery. IOLs have been very effective in correcting vision, but the implant procedure is a precise, delicate and risky surgery that, if not performed correctly, can lead to potential infection, loosening of the lens, lens rotation, inflammation, nighttime halos, and some loss to potential vision.

Many different types of IOLs are available. Each type is specifically designed to correct a certain type of eye defect or vision impairment, e.g., multifocal IOLs for simultaneous viewing of both long and near distances, and accommodating IOLs for both long and midrange near distance vision. Another type of IOL is a tonic IOL. The tonic IOL has been recently introduced to correct astigmatism in patients undergoing cataract surgery. With accurate IOL calculations and surgical technique, tonic IOLs can minimize or eliminate the need for spectacles following cataract surgery. It has been estimated that about 15-20% of patients with cataracts have astigmatism and will benefit from this lens.

To maximize the benefits of these premium lenses, accurate positioning or alignment is extremely important. The accuracy of new diagnostic tools, such as Lens Star® or IOL Master®, has contributed to the success of these lenses. When incorrectly placed, however, post-operative vision accuracy will be compromised, depending upon the degree of misalignment. For example, 15° off-axis will result in a 33% vision drop, which is not infrequent. Several studies have shown that a difference of about 10-30° of misalignment between the targeted and the achieved axis was seen in about 30-60% of the cases. Some of these cases showed a misalignment of about 45° or more. An acceptable misalignment of 5° or less was only seen in about 40% of cases. Most of these errors can be attributed to human error.

Diagnostic instruments measuring IOL power and astigmatism, such as IOL Master® or Lens Star®, are very accurate and reproducible. The discrepancy between the targeted and the achieved axis is due to identification of the proper axis, preoperative markings, and/or intra-operative misalignment. Preoperative marking of the cylinder axis is associated with significant human error. In practice, most surgeons do not have the patient in a sitting position to perform accurate axis markings. The markings are usually performed in the operating room in a semi-sitting position. With cyclotorsion, the chance of marking the axis accurately is minimal. In addition, most surgeons use methylene blue ink, which may fade by the time the patient is prepared for surgery, or the ink dilutes widely over 5-10°, which is another potential risk for error.

Intraoperative axis misalignment is mostly seen with inexperienced surgeons, which fortunately improves over time. However, chances of misalignment still exist. Due to manual rotation of the tonic IOL, centering of the IOL is not always accurate. This can cause post-op lens rotation that may lead to misalignment. Another cause of surgical error with IOL rotation is when the visco-elastic is not completely removed during surgery. This will result in clockwise rotation of the IOL. In addition to improper axis alignment, manual rotation of the tonic IOL imposes risks of capsule rupture or zonular damage in cases with weak capsule.

The current microsurgical instruments being used in this type of surgery do not appear to reduce the risks of misalignment. Most typical instruments are a type of forceps that can grab an edge of the IOL for manual rotation of the IOL. This is prone to human error, as mentioned above, with the attendant risk of capsular rupture.

In light of the above, it would be a benefit in the art of ophthalmic surgery to provide a device that can provide precise, accurate alignment of IOL with minimal risk to surrounding tissue during surgery. Thus, an intraocular lens fixation device solving the aforementioned problems is desired.

SUMMARY OF THE INVENTION

The intraocular lens (IOL) fixation device includes an elongate handle having a slender, elongate neck extending therefrom. The neck terminates at a head section. The head section includes a rotator, upon which a plurality of radiating vacuum holding legs extend outward, the end of each leg having a suction cup attached thereto. The legs and the suction cups include hollow channels that communicate with a source of vacuum in order to facilitate gripping of the IOL. Upon insertion of the IOL and proper placement of the head section over the IOL, activation of the vacuum firmly holds the IOL through the suction cups. The rotator is rotated to accurately align the IOL within the capsular bag. The IOL fixation device also includes irrigation means for selective irrigation of the target area.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
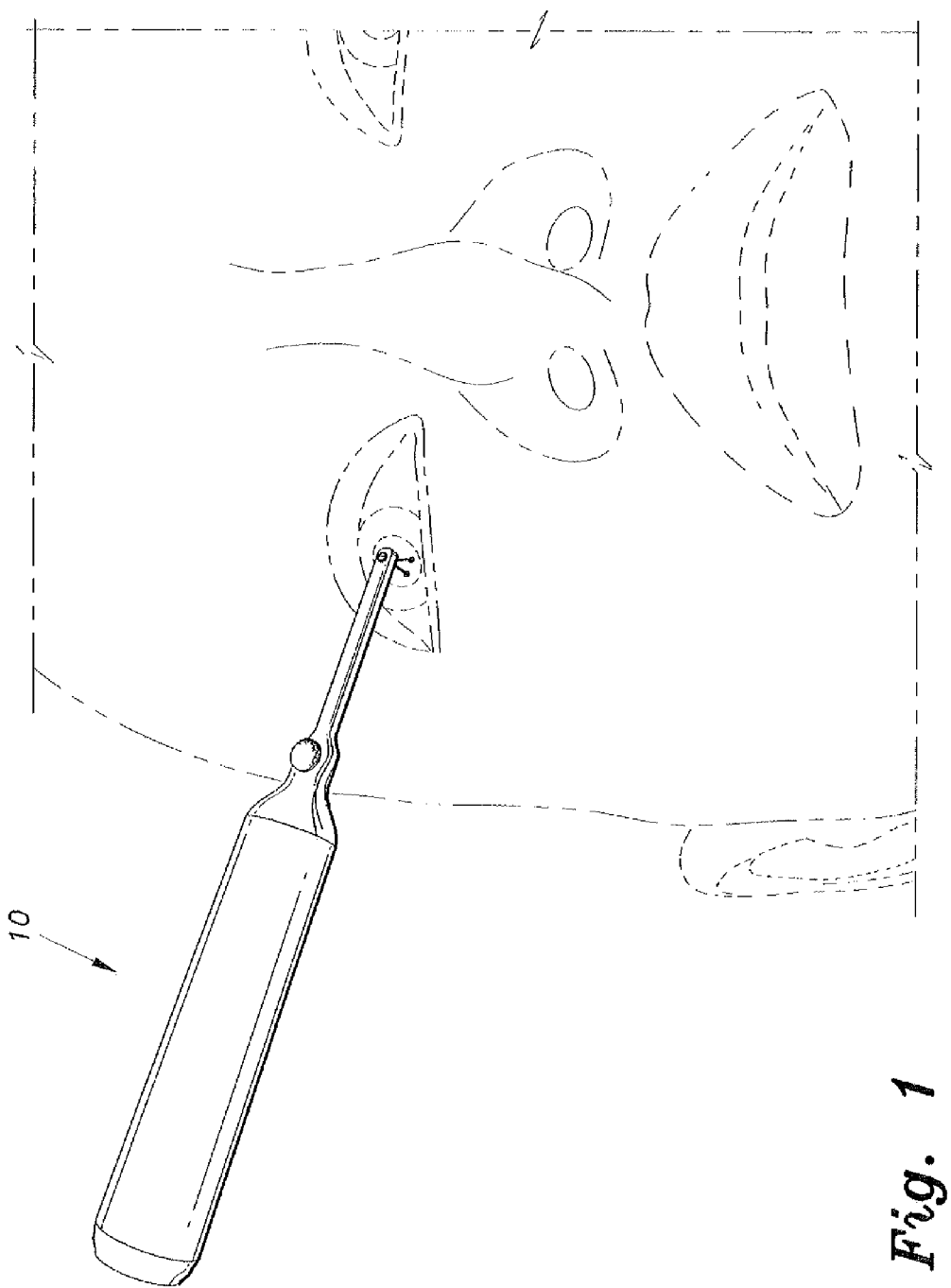
FIG. 1 is an environmental, perspective view of an intraocular lens fixation device according to the present invention.
Figure 2:
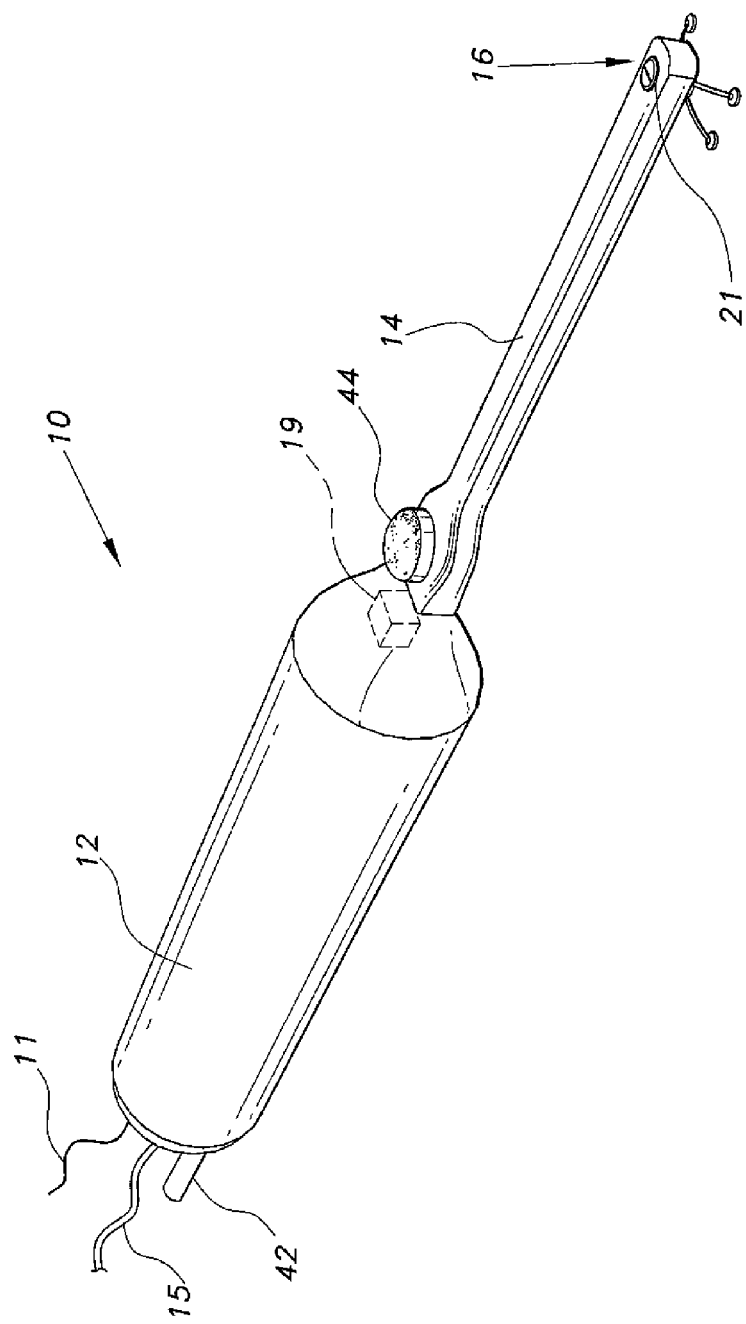
FIG. 2 is a perspective view of the intraocular lens fixation device of FIG. 1.

The intraocular lens fixation device (hereinafter referred to as an IOL fixation device), a first embodiment of which is generally referred to by the reference number 10, provides precise alignment positioning of an IOL with minimal risk to the lens capsule or capsular bag, and with minimum human error. As shown in FIGS. 1 and 2, the IOL fixation device 10 includes a housing having an elongate handle 12 that tapers at one end to an elongate neck 14. The handle 12 is preferably dimensioned to fit comfortably in the user's hand. The handle 12 can be gnarled, can have protrusions of various shapes, can be striated, can be covered or coated with friction-enhancing material, or can otherwise be configured to enhance grip. The neck 14 is preferably slender or of much smaller width or diameter than the handle 12 so that the distal end of the neck 14 can be easily manipulated during surgery.

Figure 3:
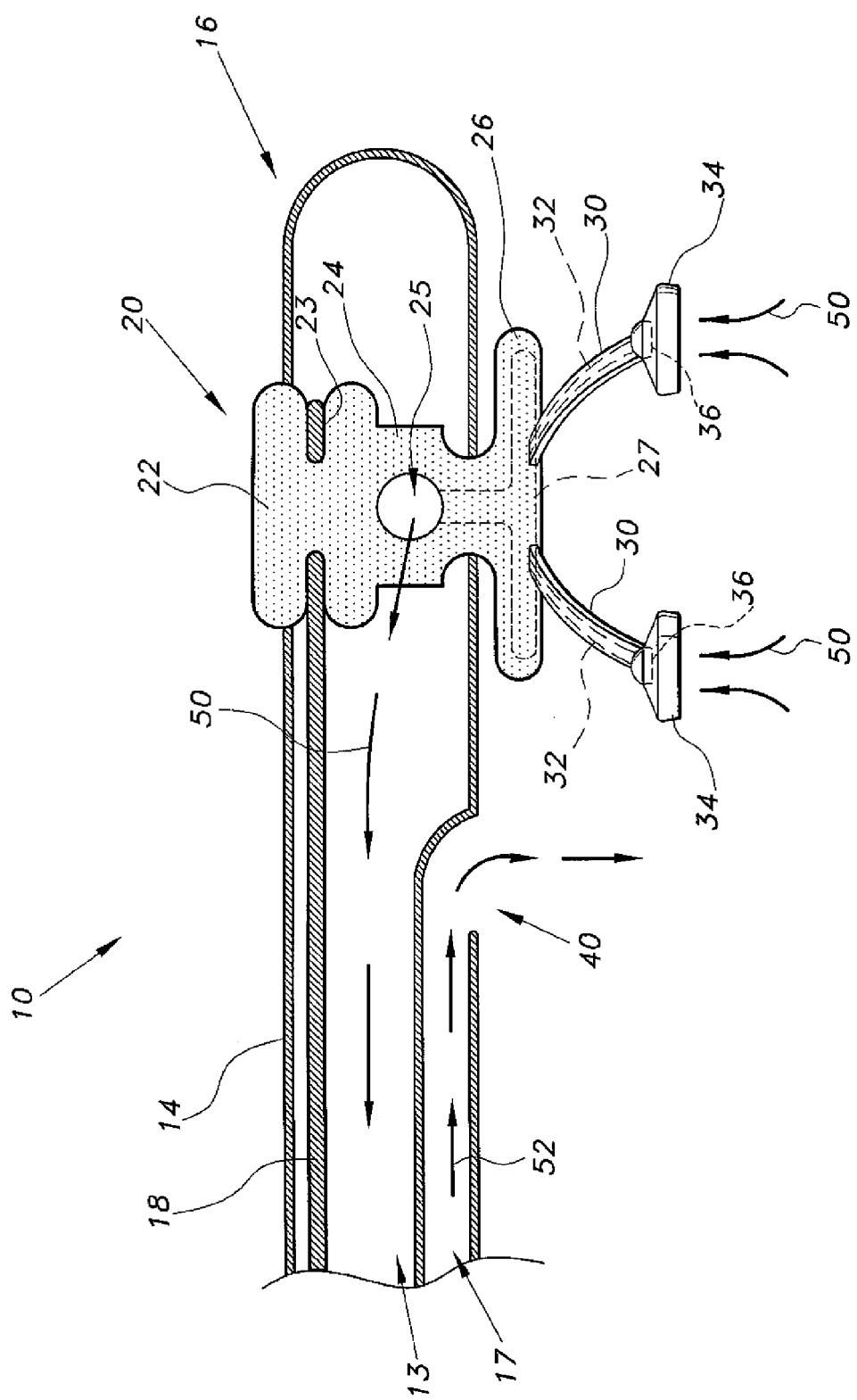
FIG. 3 is a partial side-view in section of the intraocular lens fixation device of FIG. 2, showing details of the head section.

Referring to FIGS. 2 and 3, the distal end of the neck 14 includes a head section 16, from which precise and accurate alignment of the IOL can be made. As shown, the handle 12 and neck 14 are substantially hollow. The head section 16 houses a rotator 20. The rotator 20 is preferably a single-piece unit having, from the top down in FIG. 3, a pulley wheel 22, a central support 24, and a circular disc or flange 26 extending below the bottom of the head section 16.

One end of a cable 18 is trained around a circular groove 23 formed in the pulley wheel 22, and the other end of the cable 18 is operatively attached to a motor 19 (shown in FIG. 2). A power cord 11 provides power to the motor 19. Selective activation of the motor 19 rotates the rotator 20 through the interaction of the cable 18 rotating the pulley wheel 22. The motor 19 is preferably reversible so that the rotator 20 can be rotated in the opposite direction, if required or desired by the user. Additionally, the motor 19 can be an electric or pneumatic type motor.

The central support 24 is preferably a cylindrical segment interconnected to the pulley wheel 22 and the flange 26. The central support 24 includes a throughbore or opening 25 communicating with a hollow vacuum passage 27 extending into the flange 26.

Figure 4:
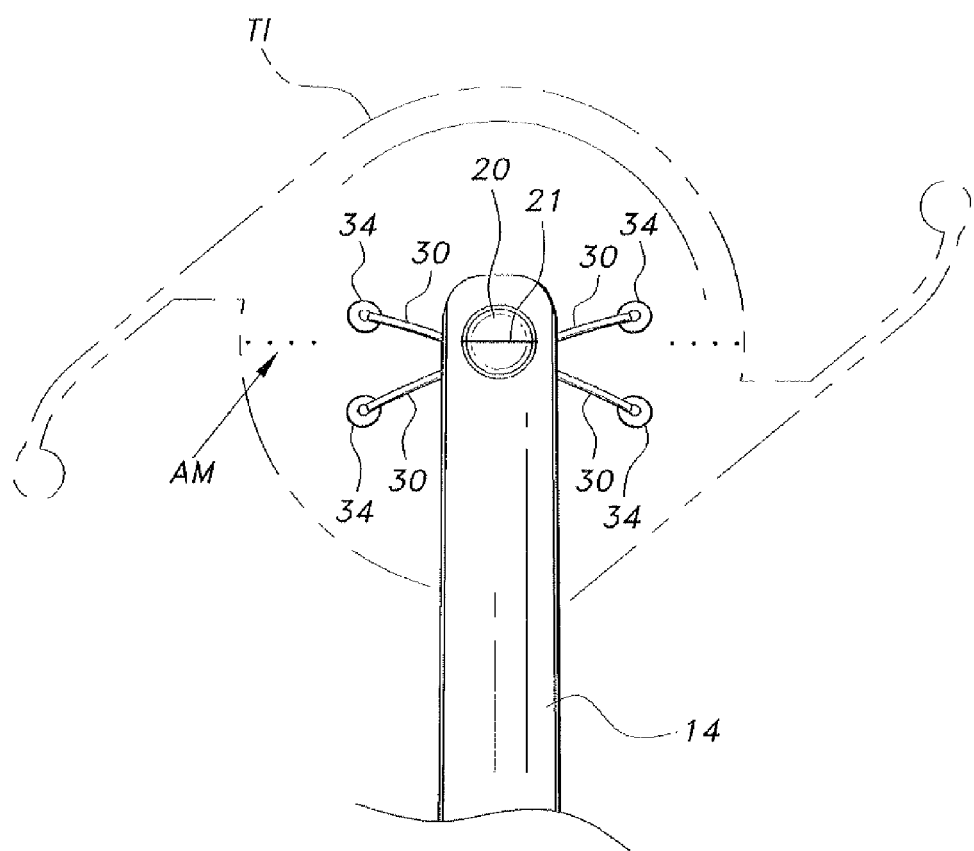
FIG. 4 is a partial top view of the intraocular lens fixation device of FIG. 1, showing the head section holding the IOL.

A plurality of vacuum holding legs 30 extend radially from the flange 26, and a suction cup 34 is attached to the distal end of each leg 30. The suction cups 34 are configured to gently but firmly hold onto the IOL TI via vacuum. The IOL fixation device 10 may, e.g., have four holding legs 30 that include two pairs of legs symmetrically spaced about the flange 26. The legs 30 of each pair are angularly spaced at an acute angle. The mid-angle of each pair defines a virtual axis therebetween. As shown in FIGS. 2 and 4, the top of the pulley wheel 22, which is exposed on top of the head section 16, includes an alignment marker or indicia 21. The alignment marker 21 is preferably a straight line or other similar indicia formed by a groove, etching, paint, or the like. This line is aligned with the virtual axis between each pair of holding legs 30. In use, the arrangement of the holding legs 30 and the alignment marker 21 provides a visual guide for the user, so that the user can properly align the IOL fixation device 10 with corresponding alignment markers AM, e.g., dots, on the tonic IOL TI as shown in FIG. 4.

The holding legs 30 are preferably constructed from flexible PMMA (polymethylmethacrylate), which is an inert form of biocompatible plastic safe for use in surgical environments. Other similar plastics can also be used. Each leg 30 is hollow and includes a channel 32 communicating with the vacuum passage 27. Similarly, each suction cup 34 includes a hollow channel 36 communicating with the channel 32 in the corresponding leg 30. The suction cups 34 are preferably constructed from soft silicon that can safely hold the IOL TI without damaging the same. The vacuum is supplied from an exterior remote source via the vacuum line 15 and the vacuum chamber 13 inside the housing. It is noted that relevant parts of the housing are sealed to insure vacuum operation.

Figure 5:
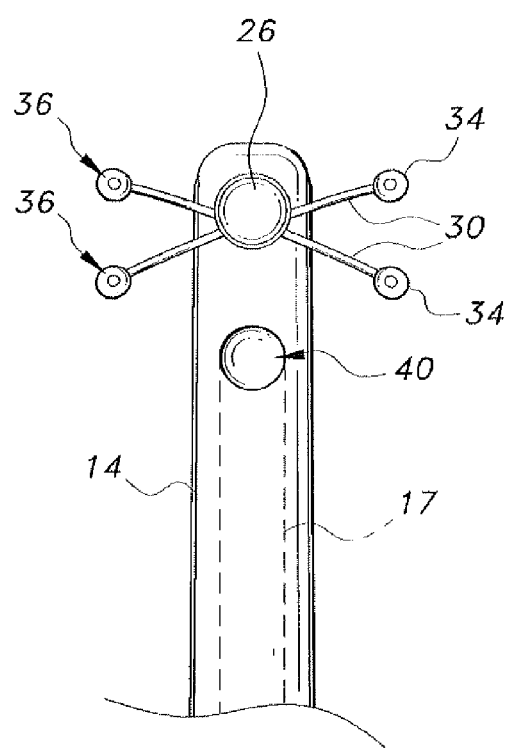
FIG. 5 is a partial bottom view of the intraocular lens fixation device of FIG. 1, showing of the head section adjusted for holding the IOL.

During this type of surgery, periodic irrigation is required to maintain anterior chamber depth in the eye. To facilitate irrigation, the IOL fixation device 10 also includes an irrigation channel 17 inside the housing communicating with an irrigation outlet or hole 40. The irrigation outlet 40 is preferably disposed proximate to, or a relatively short distance away from, the holding legs 30, as shown in FIGS. 3 and 5. This arrangement allows the user to apply irrigation fluid in situ, rather than having to re-manipulate the IOL fixation device 10 or to use a separate, remote irrigation tool. Such measures minimize potential widening of the initial incision or rupture of the lens capsule. The application of the irrigation fluid can be facilitated by a syringe mechanism 42 having an interior source of fluid (not shown) or a rear connection to a remote pump and source of fluid.

In use, the tonic IOL TI is inserted into the eye through a small incision in the usual manner, after removal of the impaired lens. An axis alignment marker based on pre-operative IOL calculations and measurements is marked or placed over the eye. Prior to insertion of the IOL fixation tool 10, the rotator 20 is rotated via selective activation of a button 44 to operate a motor that aligns the alignment marker 21 with the alignment markers AM on the IOL TI. The head section 16 is carefully inserted through the incision until the head section 16 overlies the IOL TI. Centering is performed through readjustment, as needed. Once centered, vacuum is activated to commence negative airflow, as indicated by the arrows 50 in FIG. 3. This causes the suction cups 34 to gently but firmly adhere to the surface of the IOL TI. At this point, irrigation may be applied to maintain anterior chamber depth, as indicated by the arrows 52. The rotator 20 is again activated to gently rotate the IOL TI into the proper position outlined by the axis alignment marker. Once the IOL TI is properly placed, vacuum is deactivated, and the IOL fixation device 10 is gently removed from the eye.

In contrast with conventional IOL implant procedures, the IOL fixation device 10 substantially minimizes some of the more common human errors that can occur. Throughout the above procedure, there is minimal maneuvering of the IOL fixation device 10. The major manipulation of the IOL fixation device 10 occurs mainly in the insertion and extraction of the head section 16. Meanwhile, the rotator 20 and the suction cups 34 perform the rotation for alignment, while the IOL fixation device 10 is stationary. Thus, manual rotation is eliminated. This also eliminates some of the potential rupturing of the lens capsule due to inadvertent and overt manipulation of a surgical tool by the surgeon. Moreover, a majority of the delicate and stressful repetitious handling of the conventional forceps type devices are eliminated thereby.

The above IOL fixation device 10 is an example of an automatic microsurgical tool. As briefly mentioned, the selective activation of the rotator 20 is facilitated by the button 44. The button 44 can be configured or pre-programmed with various functions. For example, a combination of button presses can be used to rotate the rotator 20 in opposite directions, or to operate the vacuum.

Figure 6:
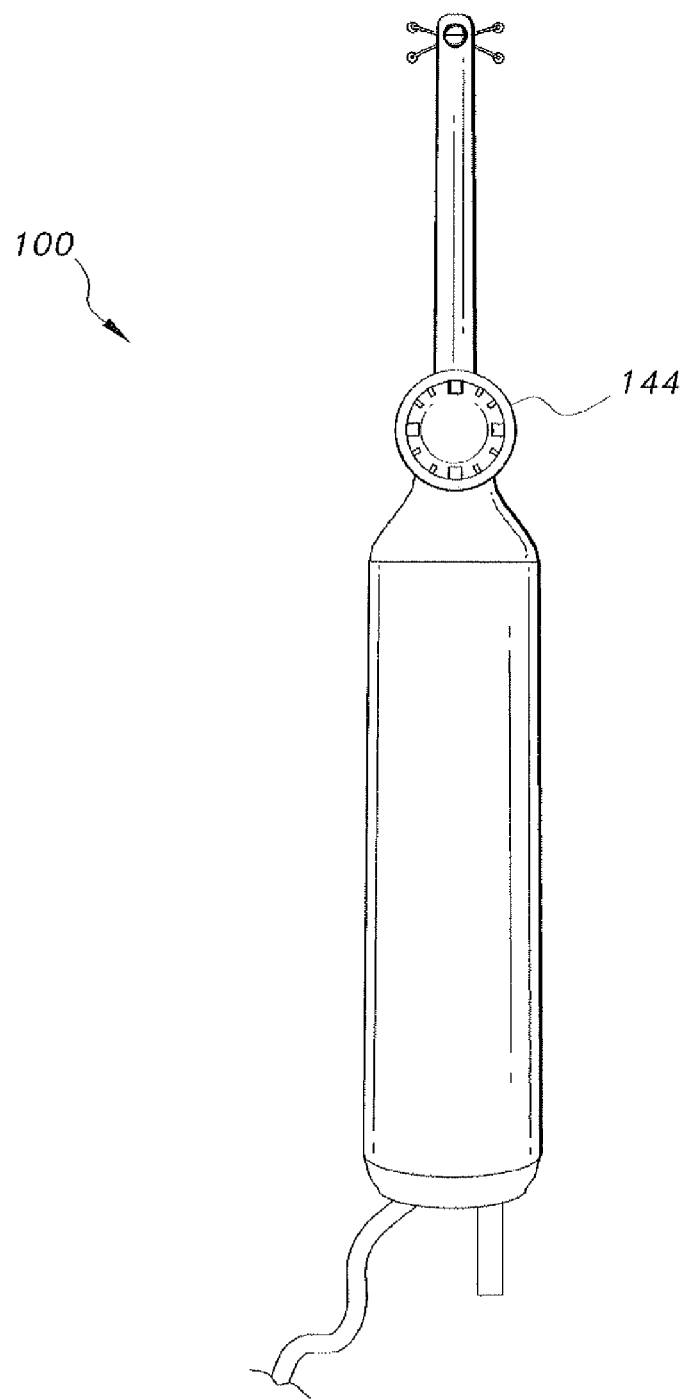
FIG. 6 is a top view of an alternative embodiment of an intraocular lens fixation device according to the present invention.

FIG. 6 discloses an alternative embodiment of an IOL fixation device 100. This IOL fixation device 100 is an example of a manual microsurgical tool, which eliminates the motor, power cord and button operation. In place thereof, the IOL fixation device 100 includes a manual dial 144 having the pulley cable 18 operatively attached thereto. The user rotates the dial 144 to rotate the rotator 20. In all other respects, the IOL fixation device 100 operates and functions substantially the same as the IOL fixation device 10.

It is to be understood that the IOL fixation device 10, 100 encompasses a variety of alternatives. For example, the IOL fixation device 10, 100 can be constructed from surgical grade plastics, metals, composites and/or combinations thereof. The IOL fixation device 10, 100 can also include selectively operable LED lights for illuminating target areas during surgery. The IOL fixation device 10, 100 can also be operatively connected to precision imaging and adjusting devices, such microscopes and computers, to assist alignment procedures.

It is to be understood that the present invention is not limited to the embodiments described above, but encompasses any and all embodiments within the scope of the following claims.

I claim:

1. An intraocular lens (IOL) fixation device, comprising:
 a hollow housing having an elongate handle and an elongate neck extending from the handle, the neck having a width smaller than the handle, the housing having an interior vacuum chamber;
 a head disposed at the end of the neck distal from the handle;
 a rotator housed in the head, the rotator being selectively rotatable, the rotator having a plurality of vacuum holding legs extending radially therefrom, each of the legs having a distal end and a suction cup attached to the distal end of the leg;
 a selectively operable vacuum source operatively attached to the housing; and
 an irrigation means for irrigating the eye to maintain anterior chamber depth of a lens capsule during an IOL implant operation;
 wherein selective activation of the vacuum source facilitates gentle and firm gripping of the IOL by the suction cups, and selective rotation of the rotator rotationally aligns the IOL into a desired proper position during the implant operation with minimal repositioning of the IOL fixation device.

2. The IOL fixation device according to claim 1, wherein said rotator comprises:
 a pulley wheel having a top face exposed on top of the head, the pulley wheel having a circular cable groove;
 a central support attached to the pulley wheel, the central support having an opening communicating with said vacuum chamber; and
 a flange extending from the central support, said plurality of holding legs extending from the flange, the flange having an interior vacuum passage communicating with the opening in the central support.

3. The IOL fixation device according to claim 2, wherein said plurality of holding legs comprises four vacuum holding legs, each of the vacuum holding legs having an interior hollow channel, each said suction cup having an interior channel, the channel of said each of the legs having one end communicating with the vacuum passage in said flange and an opposite end communicating with the corresponding interior channel in said suction cup, the channels of said legs and said suction cups facilitating flow of vacuum upon activation thereof.

4. The IOL fixation device according to claim 3, wherein said four vacuum holding legs include two pairs symmetrically and angularly spaced about said flange, each pair of said legs defining an acute angle, the acute angles being opposite angles defining a virtual axis therebetween.

5. The IOL fixation device according to claim 4, wherein the top face of said pulley wheel has an alignment marker disposed thereon, the alignment marker being in alignable with the virtual axis, the alignment marker forming a visual aid for aligning said holding legs with alignment markers on said IOL.

6. The IOL fixation device according to claim 2, further comprising:
 a cable having one end trained around the cable groove on said pulley wheel; and
 an actuator for selective rotation of said rotator, the cable having an opposite end operatively attached to the actuator.

7. The IOL fixation device according to claim 6, wherein said actuator comprises a motor disposed in said housing and a button disposed on the housing and connected to the motor for selective activation of the motor.

8. The IOL fixation device according to claim 6, wherein said actuator comprises a manual dial.

9. The IOL fixation device according to claim 1, wherein said irrigation means comprises an irrigation channel disposed in the housing; an irrigation outlet at one end of said irrigation channel; and an irrigation syringe connected to the irrigation channel opposite the outlet end.

10. The IOL fixation device according to claim 9, wherein said irrigation outlet is disposed proximate said vacuum holding legs.

11. The IOL fixation device according to claim 1, wherein said vacuum holding legs are constructed from flexible polymethylmethacrylate (PMMA).

12. The IOL fixation device according to claim 1, wherein said suction cups are constructed from soft silicon.

* * * * *